United States Patent [19]

Chen et al.

[11] Patent Number: 4,740,459
[45] Date of Patent: Apr. 26, 1988

[54] FLUORESCENCE ASSAY FOR MICROBIAL BETA-LACTAMASE

[75] Inventors: Kirk C. S. Chen; Florence J. Knapp; King K. Holmes, all of King County, Wash.

[73] Assignee: Washington Research Foundation, Seattle, Wash.

[21] Appl. No.: 638,012

[22] Filed: Aug. 6, 1984

[51] Int. Cl.$^4$ .......................... C12Q 1/34; C12Q 1/18
[52] U.S. Cl. ....................... 435/18; 435/32; 435/805
[58] Field of Search ...................... 435/18, 29, 32, 33, 435/34, 39, 805

[56] References Cited

U.S. PATENT DOCUMENTS 4,381,343  4/1983  Citri .................................. 435/32 X

FOREIGN PATENT DOCUMENTS

WO80/02295 10/1980 European Pat. Off. .............. 435/34

OTHER PUBLICATIONS

Anderson, E. G. et al., *J. Biol. Chem.*, vol. 258, No. 21, 1983, pp. 13120–13126.
Chen, K. C. S. et al., *J. Clin. Micro.*, vol. 19, No. 6, 1984, pp. 818–825.
Wolfson, J. S. et al., *Antimicrob. Agents and Chemother.*, vol. 23, 1983, pp. 308–312.
Bae, B. H. C. et al., *J. Clin. Microb.*, vol. 17, 1983, pp. 545–547.

*Primary Examiner*—Esther M. Kepplinger
*Assistant Examiner*—Jeremy M. Jay
*Attorney, Agent, or Firm*—Seed and Berry

[57] ABSTRACT

A rapid method for the specific detection of the presence of Beta-lactamase from microbial sources is disclosed. The method utilizes a Beta-lactam ring containing substrate whose amide bond is hydrolyzed in the presence of Beta-Lactamase. A substrate, which includes a Beta-Lactam antibiotic with an acyl side chain containing an α-amino group and a α-phenyl group and/or its derivatives is first contacted with an organism thought to produce Beta-lactamase or a cell-free Beta-lactamase preparation, and, subsequently, it is determined whether the reaction product between the substrate and the organism or the preparation fluoresces.

27 Claims, 4 Drawing Sheets

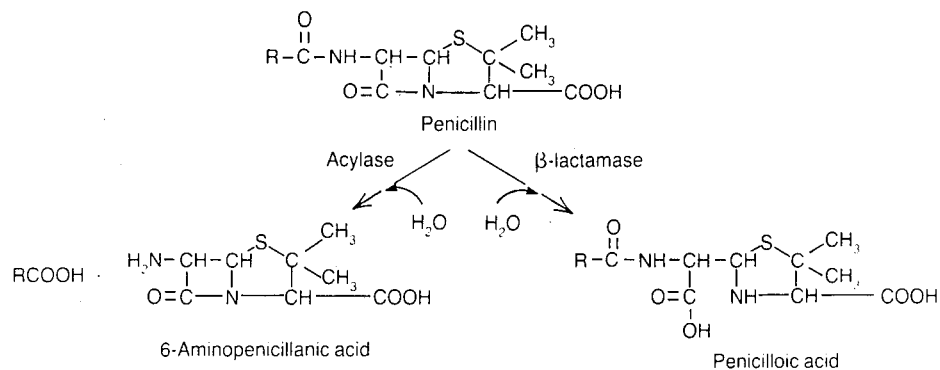
FIG. 1
FIG. 2
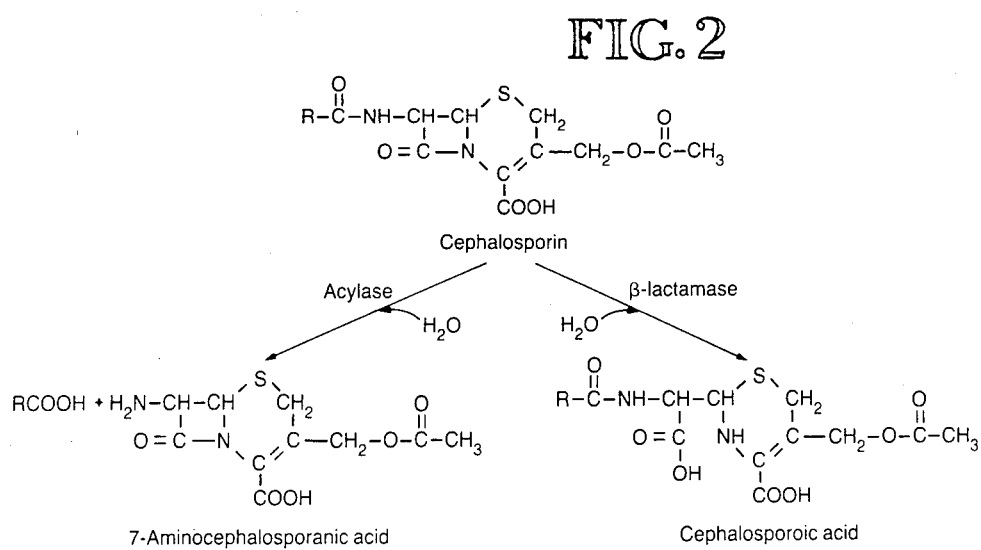

| Nonfluorescent substrate | Hydrolysis | Fluorescent product | Fluorescence development | Long-wave UV lamp |
|---|---|---|---|---|
| Ampicillin (50 μl, 0.02 M, pH 7.0) | 1/2 loopful of bacteria ⟶ Penicillinase activity | D-Phenylglycyl-penicilloic acid | 5 μl on paper ⟶ 120°C, 5 min | Fluorescence |
| Cephalexin (50 μl, 0.02 M, pH 7.0) | 1/2 loopful of bacteria ⟶ Cephalosporinase activity | D-Phenylglycyl-deacetoxycephalo-sporoic acid | 5 μl on paper ⟶ 120°C, 5 min | Fluorescence |

Summary of the fluorescent spot test for detection of microbial β-lactamases.

FIG. 4

FLUORESCENCE ASSAY FOR MICROBIAL BETA-LACTAMASE

DESCRIPTION

The invention described herein was made in the course of work under Public Health Service Research Program Project grant Al-12192 from the National Institutes of Health.

TECHNICAL FIELD

This invention relates to a rapid method for the specific detection of the presence of Beta-lactamase from microbial sources and to a method of differentiating penicillinase activity from cephalosporinase activity.

BACKGROUND ART

Beta-lactamases which hydrolyze the amide bonds of the Beta-lactam ring of sensitive penicillins and cephalosporins are widely distributed among microorganisms, and play an important role in microbial resistance to Beta-lactam antibiotics. Several methods for detecting the presence of microbial Beta-lactamase have been developed. For example, chemical methods for the detection of the enzymatic hydrolysis of the Beta-lactam ring include: (a) the acidimetric method, which employs a pH color indicator to detect the decrease in pH resulting from the formation of a new carboxyl group; (b) the iodometric method, which is based on the decolorization of a starch-iodine complex by the end products of Beta-lactamase hydrolysis, which act as reducing agents to reduce iodine in the complex; and (c) the chromogenic cephalosporin method which is based on a color change following the hydrolysis of a chromogenic cephalosporin substrate (R. B. Sykes and K. Bush, "Physiology, Biochemistry and Inactivation of Beta-lactamases"; *Chemistry and Biology of Beta-lactam Antibiotics,* Vol. 3: 155–207 1982 Academic Press, New York, R. B. Morin and M. Gorman, Editors). An alternative to the chemical methods is a microbiological assay method which is based on the loss of antibacterial activity following the hydrolysis of the Beta-lactam ring.

Microbial acylases which remove the acyl side chains of susceptible penicillins or cephalosporins are also produced by many microorganisms. The cleavage of acyl side chains from Beta-lactam antibiotics often results in a decrease in pH and reduction of antibiotic activity.

Although microbial Beta-lactamases do not act exclusively on penicillins or on cephalosporins, many show a predominance of penicillinase or cephalosporinase activity. Thus, chemical or microbiological methods which utilize a single Beta-lactam substrate cannot differentiate penicillinase activity from cephalosporinase activity and often give a false negative result for Beta-lactamase activity.

There exists a need for a method which differentiates penicillinase activity from cephalosporinase activity and distinguishes between Beta-lactamase and acylase activity. The present invention fulfills this need and provides other advantages; principally, that of providing an economical alternative to clinical laboratories which test large numbers of microorganisms for Beta-lactamases compared with methods presently available.

DISCLOSURE OF THE INVENTION

Briefly stated, the present invention comprises a method for specifically detecting the presence of Beta-lactamase from microbial sources, while concurrently providing a method of differentiating pencillinase from cephalosporinase activity.

The method includes contacting a Beta-lactam ring containing substrate with an organism thought to produce Beta-lactamase or a cell-free Beta-lactamase preparation and then subsequently determining whether the reaction product between the substrate and the organism or the preparation fluoresces, fluorescence being an indicator of the presence of Beta-lactamase.

The substrate may include a Beta-lactam antibiotic with an acyl side chain containing an α-amino group and an α-phenyl group and/or its derivatives, such as cyclohexyl or cyclohexenyl, including hydrohexyl and hydrohexenyl. For example, the acyl side chain of the Beta-lactam antibiotic may contain a D (−) α-phenylglycyl group such as ampicillin, cephalexin, or cephaloglycin (phenyl group without substitution), or a D (−)-p-hydroxyphenylglycyl group such as amoxicillin or cefadroxil (phenyl group with hydroxyl group substitution).

The reaction mixture after incubation of the substrate and organism or a cell free Beta-lactamase preparation may be placed onto a surface with low background fluorescence, such as filter paper, and fluorescence developed by briefly heating the reaction mixture on the surface.

This same method can differentiate Beta-lactamase activity from acylase activity since Beta-lactamase activity towards a Beta-lactam antibiotic with an acyl side chain as described above generates fluorescent endproducts, while acylase activity produces nonfluorescent end-products.

In addition, as noted above, by using Beta-lactam substrates representing both penicillin and cephalosporin antibiotics, the specificity of Beta-lactamases of various species of gram-positive and gram-negative bacteria may be determined. For example, one can determine whether penicillinase and/or cephalosporinase activity is present in an organism by contacting the organism suspected of producing Beta-lactamase with ampicillin or amoxicillin (for penicillinase activity), determining whether fluorescence is present or absent within the resulting reaction product, and carrying out a similar test with cephalexin, cefadroxil or cephaloglycin (for cephalosporinase activity).

An alternative embodiment which allows the detection and differentiation of the fluorescent end-product initiated by the presence of Beta-lactamase activity from the natural fluorescence of a strain of bacteria on milieu comprises impregnating an interface layer, such as filter paper, with a Beta-lactam substrate as described above whose amide bond is hydrolyzed in the presence of Beta-lactamase, subsequently placing the interface layer containing the substrate in contact with the surface of the culture medium, and then determining whether the reaction product between the substrate and the bacteria fluoresces.

BRIEF DISCRIPTION OF THE DRAWINGS

FIG. 1 diagrammatically illustrates the hydrolysis of penicillins by acylase and Beta-lactamase.

FIG. 2 diagrammatically illustrates the hydrolysis of cephalosporins by acylase and Beta-lactamase.

FIG. 4 is a summary of the fluorescent spot test for the detection of microbial Beta-lactamases.

BEST MODE FOR CARRYING OUT THE INVENTION

Figure 3:
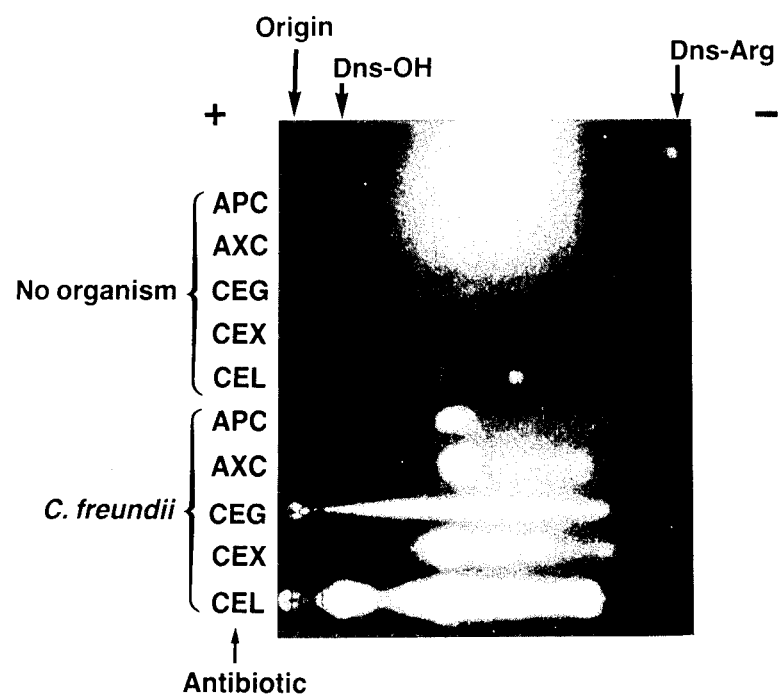
FIG. 3 depicts high voltage electrophoretic analysis of open Beta-lactam ring end products.

As noted above, Beta-lactamases which hydrolyze the amide bonds of the Beta-lactam ring of sensitive penicillins and cephalosporins play an important role in microbial resistance to Beta-lactam antibiotics. While the various chemical and microbiological assay methods previously mentioned have been useful for detecting microbial Beta-lactamases, they are somewhat deficient in sensitivity and are relatively expensive in comparison to the improved method disclosed herein.

This invention provides a more sensitive and less expensive method for detecting microbial Beta-lactamases which can not only differentiate penicillinase from cephalosporinase activity but can also differentiate Beta-lactamase activity from acylase activity. Some penicillins and cephalosporins, such as ampicillin and cephalexin, yield fluorescent end-products after hydrolysis by Beta-lactamase. Further, these fluorescent end-products can be detected on filter paper under a long wave ultra violet light lamp after brief heating.

Consistent with these findings, an assay for the detection of microbial Beta-lactamases with a predominance of either penicillinase or cephalosporinase activity may be initiated by: (a) uncubating an amount of a solution of a Beta-lactam antibiotic such as ampicillin or cephalexin, or other Beta-lactam containing as side chain with an α-amino group and an α-phenyl group with or without various substitutions with a test microorganism thought to produce Beta-lactamase or a cell-free Beta-lactamase preparation; (b) placing a drop of that solution on a surface, such as filter paper; (c) briefly heating the filter paper; and (d) exposing the filter paper to fluorescent light.

Other Beta-lactams which may be utilized include amoxicillin, cephaloglycin, and cefadroxil.

Suitable surfaces with low background fluorescence other than filter paper include paper towels, sheets of nitrocellulose, cellulose acetate, silica gel or polyamide.

This method may be used to detect predominant penicillinase activity (e.g., using ampicillin or amoxicillin as the substrate) or cephalosporinase activity (e.g., using cephalexin, cefadroxil, or cephaloglycin as the substrate). Since Beta-lactamase activity towards ampicillin and cephalexin generates fluorescent end-products (D-phenylglycylpenicilloic acid and D-phenylglycyl-deacetoxycephalosporic acid) and acylase activity produces nonfluorescent end-products [D-(−)-α-aminophenylacetic acid, 6-aminopencillanic acid and 7-aminodeacetoxycephalosporanic acid] as shown in the FIGS. 1, 2, 5 and 6, Beta-lactamase activity may be distinguished from acylase activity.

The presence of acylase in the reaction mixture does not interfere with the detection of Beta-lactamase using this fluorescent method. By using Beta-lactam substrates representing both penicillin and cephalosporin antibiotics, the specificity of Beta-lactamases of various species of gram-positive and gram-negative organisms can be determined.

An alternative method employing an overlay which has been impregnated with the Beta-lactam substrate, contacted with the bacteria on the surface of a culture medium, incubated, and then viewed under a long wave ultra-violet light lamp to detect the fluorescence, has also been developed, permitting the detection and differentiation of the fluorescence end-product from the natural fluorescence of the bacteria without the need for removing the bacteria from the milieu through centrifugation, while in addition allowing the detection of enzyme activity by many individual colonies on one plate.

It will be appreciated by those skilled in the art through reference to the examples which follow that slight variations on the assay disclosed will readily exist, depending for instance, on the activity of the enzyme and the sample being tested.

For example, the reaction mixture composed of the source of Beta-lactamase suspended only in the ampicillin substrate solution may be examined immediately without further incubation for fluorescence produced by plasmid mediated Beta-lactamases (e.g. penicillinase producing *Neisseria gonorrhoeae, Haemophilus influenzae*), or may be incubated with either ampicillin or cephalexin prior to examination, for fluorescence produced by inducible Beta-lactamases or by weak Beta-lactamase producers.

To summarize the example which follows, detection of open Beta-lactam ring end-products was accomplished utilizing the rapid detection method or spot test of this invention confirming the spot test results with a highvoltage electrophoresis (HVE) test; and then also confirming the spot test by the nitrocefin test.

The results obtained through the use of these procedures revealed that (1) Beta-lactamase may be detected through identification of fluorescent end-products utilizing the rapid spot test without the necessity of electrophoretic separation of the substrates and end products; (2) the spot test proved to be more sensitive than the nitrocefin test, especially for gram-positive microorganisms; (3) the rapid detection method or spot test can be utilized to differentiate between penicillinase and cephalosporinase activities, as well as differentiating Beta-lactamase activities from acylase activities; (4) the spot test provides a means of semi-quantitatively determining the amount of beta-lactamase activity from a microbial source; and (5) the spot test method may be utilized to determine the specificity of Beta-lactamases of various species of gram-positive and gram-negative bacteria.

All references noted through citation of the example which follows are hereby incorporated by reference as if their text had been fully set forth herein.

The following examples are offered by way of illustration and not by way of limitation.

EXAMPLE

Materials

Chemicals. Compounds (acid forms) related to Beta-lactam antibiotics, including the acyl side chain and the Beta-lactam nuclei, were purchased from Sigma Chemical Co., St. Louis, MO, and separately dissolved in 0.04M sodium phosphate buffer, pH 7.5, to a final concentration of 0.02M, except for amoxicillin (0.01M, prepared in 0.02M sodium phosphate buffer) and D(—)-α-aminophenylacetic acid (0.005M, prepared in 0.01M sodium phosphate buffer). Nitrocefin was obtained from Glaxo Research Ltd., Greenford, Middlesex, England and was prepared and used at a concentration of 50 ug/ml. (Sykes, R. B., and K. Bush. 1982. Physiology, biochemistry, and inactivation of Beta-lactamases, p. 155–207; *Chemistry and biology of Beta-lactam antiobiotics*, Vol. 3. R. B. Morin and M. Gorman (ed.), Academic Press, New York).

Methods

Preparation of inocula for detection of Beta-lactamase.

*Haemophilus ducreyi* and *H. influenzae* were grown on GC agar base (BBL Microbiology Systems, Cockeysville, Md) with supplements as described in Totten, P. A., H. H. Handsfield, D. Peters, K. K. Holmes, and S. Falkow Characterization of ampicillin resistance plasmids from *Haemophilus ducreyi*. Antimicrob. Agents Chemother. 21: 622–627 1982. Bacteroides spp. were grown anaerobically on Columbia base gear (BBL) with supplements as described in Williams, B. L., K-A Osterberg, and J. Jorgensen, Subgingival microflora of periodontal patients on tetracycline therapy. J. Clin. Periodontol. 6: 210–221 1979. Microorganisms from research efforts described previously in Chen, K. C. S., N. J. Culbertson, J. S. Knapp, G. E. Kenny and K. K. Holmes, Rapid method for simultaneous detection of the arginine dihydrolase system and amino acid decarboxylases in microorganisms; J. Clin. Microbiol. 16: 909–918 1982, were grown aerobically on GC medium base (Difco Laboratories, Detroit, MI) containing 1% defined supplement (White, L. A., and D. S. Kellogg Jr. *Neisseria gonorrhoeae* identification in direct smears by a fluorescent antibody counterstain method. Appl. Microbiol. 13: 171–174 1965at 37° C. overnight, except for *Neisseria gonorrhoeae*, which was grown in a $CO_2$ incubator (Totten, P. A., H. H. Handsfield, D. Peters, K. K. Holmes, and S. Falkow. Characterization of ampicillin resistance plasmids from *Haemophilus ducreyi*. Antimicrob. Agents Chemother. 21: 622–627 1982.

Aliquots (50 ul) of each Beta-lactam antibiotic were separately place in a microcentrifuge tube (200 ul; Stockwell Scientific, Monterey Park, Ca). Approximately one-half of a loopful (diameter, 2 mm) of growth of each strain was removed from the agar plate and dispensed in each substrate by brief vortexing.

The mixture was then incubated for 5 and 15 minutes at room temperature for the rapid spot test. Uninoculated substrate controls were prepared in the same manner.

Concurrently, the mixture of the strain and each substrate was incubated for 1 hour at 37° C. Uninoculated substrate controls were again prepared in the same manner. After incubation, the tubes (except the uninoculated substrate control tubes and tubes for the rapid spot test) were centrifuged in a Microfuge (model 15; Beckman Instruments, Inc., Fullerton, CA) for 1 minute.

Detection of open Beta-lactam ring end products by the spot test.

After 1 h incubation at 37° C., a 5 ul volume of supernatant for each tube, including each uninoculated substrate control tube, was applied separately onto a Whatman 3 MM paper and heated at 120° C. in an oven for 5 min. The fluorescent intensity of each test spot was then compared with the control spot of its uninoculated substrate under a long-wave uv lamp and classified as negative, weakly positive, or positive.

For the rapid spot test, 5 ul of uncentrifuged bacterial suspension from each inoculated tube after incubation at room temperature for 5 min or 15 min, and 5 ul from each uninoculated substrate control tube, were applied onto the paper and heated at 120° C. for 5 min. For microorganisms which showed strong autofluorescence (e.g., Pseudomonas spp.), the tip of an Eppendorf pipettor containing 5 ul of suspension was applied to the filter paper, allowing the fluid to be withdrawn from the tip by capillary action. This caused the bacteria to remain concentrated at the point of application, so that central bacterial autofluorescence could be differentiated from peripheral fluorescence of the end products. The fluorescent intensity of the rapid spot test was classified as described for the 1 h spot test.

Detection of open Beta lactam ring end products by high-voltage electrophoresis.

A 5 ul volume of supernatant from each tube after 1 h incubation was separately applied onto a Whatman 3 MM paper which was subjected to high-voltage electrophoresis (HVE) at pH 2.1, at 80 V/cm for 30 min. (Chen, K. C. S., and R. M. Krause, A peptide mapping technique—a three map system. Anal. Biochem. 69: 180–186 1975). The paper was dried at 90° C. for 15 min., and viewed under a long-wave uv lamp. The fluorescent intensity of each test was compared with that of its uninoculated substrate control and classified as negative, weakly positive or positive. The paper was then stained with ninhydrin-cadmium acetate (Heilmann, J., J. Barrollier, and E. Watzke, Beitrag zur Aminosaurebestimung auf Papierchromatogrammen. Hoppe-Seyler's Z. Physiol. Chem. 309: 219–220 1975), to reveal the unhydrolyzed substrate. The color intensities of the end-products were further classified as negative, or as weakly, or moderately, or strongly positive.

Detection of Beta-lactamase by the nitrocefin test

The nitrocefin test (O'Callaghan, C. H., A. Morris, S. M. Kirby, and A. H. Shingler, Novel method for detection of Beta-lactamases by using a chromogenic cephalosporin substrate, Antimicrob. Agents Chemother. 1: 283–288 1972), it is a specific and one of the most rapid tests available for the detection of Beta-lactamase and was performed concurrently with the rapid detection method or spot test described herein in order to provide means for evaluating the accuracy of the spot test.

The nitrocefin test was performed under the same conditions as the spot test. Approximately one-half of a loopful of growth of each organism was dispersed in 50 ul of nitrocefin (50 ug/ml) in a well of a microtitration plates (Linbro Division, Flow Laboratories, Inc., Hamden, Conn.), and incubated for 1 h at 37° C., or for 5 and 15 min. at room temperature for the rapid test.

Detection of Beta-lactamase by identification of fluorescent end products.

In initial studies, penicillins (ampicillin and amoxicillin) and cephalosporins (cephalosporin C, cephaloglycin, cephalexin and cefadroxil) containing a primary amino group on the acyl side chain were separately incubated with *Citrobacter freundii* for 1 h at 37° C. Supernatant from each reaction mixture was separated by HVE (high voltage electrophoresis) at pH 2.1 (Chen, K. C. S., and R. M. Krause, A peptide mapping technique—a three map system. Anal. Biochem. 69 180–186 1975). The product and the unhydrolyzed substsrate were revealed by ninhydrin-cadmium acetate stain (Heilmann, J., J. Barrollier, and E. Watzke, Beitrag zur Aminosaurebestimung auf Papier Chromatogrammen. Hoppe Seyler's Z. Physiol. Chem. 309: 219–220 1975), after drying at 90° C. for 15 minutes. The ninhydrin-cadmium acetate stain showed distinct spots of the end-product and the unhydrolyzed substrate for all Beta-lactam antibiotics tested except cephaloglycin and cephalosporin C (the end products trailed toward the cathode).

Subsequent studies showed that prior to ninhydrin-cadmium acetate staining, each major end-product (as detected later by ninhydrin-cadmium stain; cephaloglycin produced no distinct major end-product) and some minor end-products, except from cephalosporin C, were highly fluorescent under a long-wave uv lamp, while the unhydrolyzed substrates were not fluorescent as shown in FIG. 3. The fluorescent pattern produced by *C. freundii* for each substrate was found to be identical to that produced by purified Beta-lactamase from *Enterobacter cloacae* or *Bacillus cereus* (Sigma; 100 nanomoles of each substrate incubated with 1 ug of each enzyme for 1 h at 37° C.). Trace amounts of the fluorescent open Beta-lactam-ring forms of ampicillin, amoxicillin, and cefadroxil detected in the uninoculated substrate control were attributable to spontaneous hydrolysis during incubation and contamination with the open-ring-forms themselves in the commercial sources, and this background of fluorescence was easily distinguished from the amount of fluorescent end-product produced by the microbial Beta-lactamases. The minor fluorescent end-products of cephalexin and cefadroxil after incubation were presumably due to acid degradation of each major end-product during HVE at pH 2.1, since better cooling of paper during HVE reduced their formation. Therefore, all five Beta-lactam substrates which produced fluorescent end products (open Beta-lactam-ring forms) during incubation with known Beta-lactamases could be used for detection of microbial Beta-lactamases.

In addition, it was also found that the end product of each Beta-lactam substrate shown in FIG. 3 could be detected on the filter paper without subsequent electrophoretic separation after brief heating at 120° C. for 5 minutes. Therefore, the simple spot test described herein can be employed for the detection of microbial Beta-lactamases.

Selection of Beta-lactam substrates for differentiation between penicillinase and cephalosporinase activites of Beta-lactamase by the spot test.

In order to detect Beta-lactamases with a predominance of penicillinase or cephalosporinase activity, and to detect weak Beta-lactamase producers using the spot test, two substrates which produced the least fluorescent background (due to nonenzymatic hydrolysis during incubation and the end product contaminants present in the commercial sources) were selected. Ampicillin produced less fluorescent background than amoxicillin, and was chosen as the substrate for penicillinase despite the fact that its open Beta-lactam-ring form was less fluorescent than that of amoxicillin as shown in FIG. 3. Likewise, cephalexin was chosen as the substrate for cephalosporinase. A summary of the fluorescent spot test method is provided in FIG. 4.

Differentiation of Beta-lactamase and acylase activites by the spot test and HVE.

Figures 5, 6:
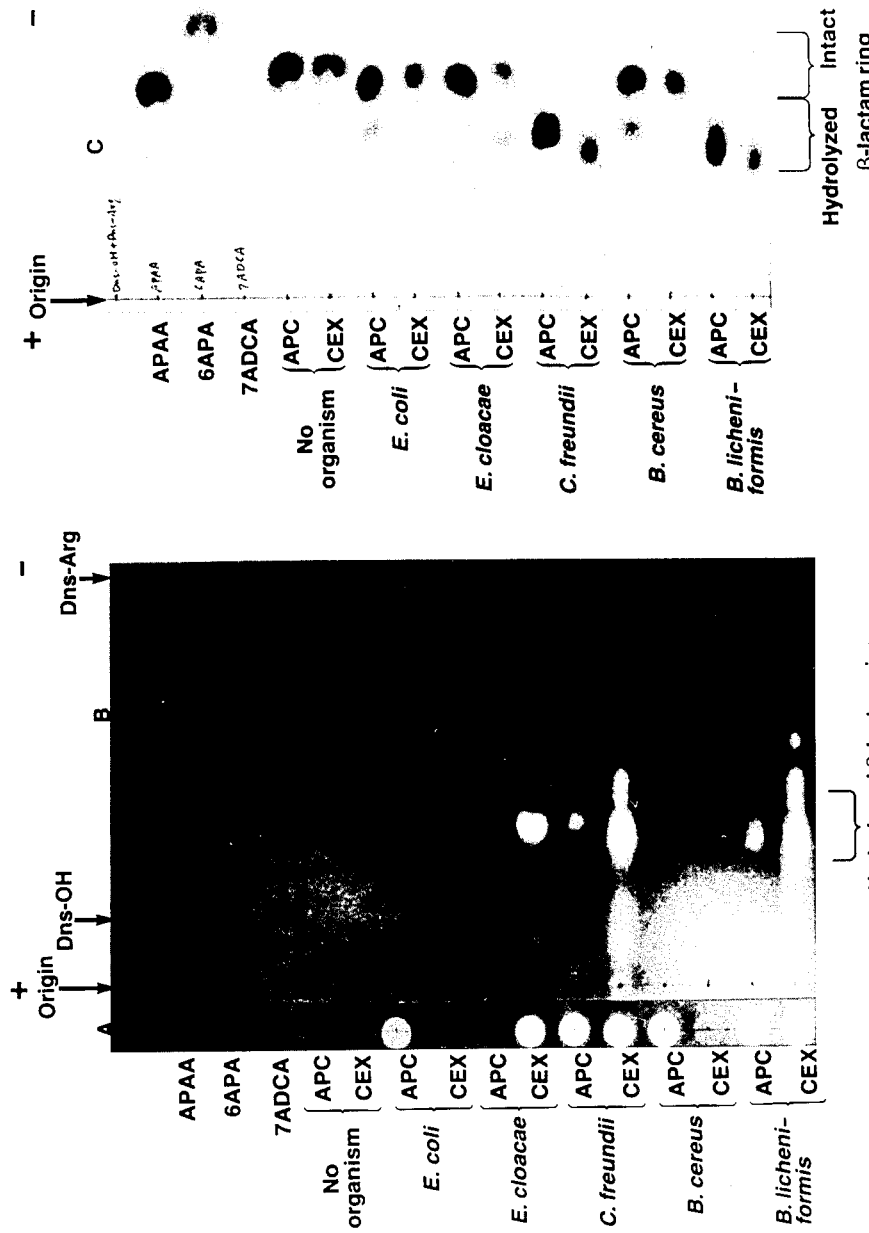
FIG. 5 illustrates the activity of Beta-lactamase in *E. coli, E. cloacae, C. freundii, B. cereus,* and *B. licheniformis* as determined by the spot test (A) and the high voltage electrophoresis test (B) viewed under a long wave UV lamp.
FIG. 6 illustrates the activity of Beta-lactamase as depicted in FIG. 5 after ninhydrin-cadmium acetate staining.

In order to determine whether the spot test method could distinguish Beta-lactamase activity from acylase activity, the end products of acylase, (100 nanomoles each, the common side chain, D(−)-α-aminophenylacetic acid, and the intact Beta-lactam nuclei, 6-aminopenicillanic acid and 7-aminodeacetoxycephalosporanic acid) were separately applied onto Whatman 3 MM paper. None of the end-products of acylase were fluorescent either by the spot test method or the HVE method as shown in FIG. 5. However, all produced color after ninhydrin-cadmium acetate stain as shown in FIG. 6. Therefore, both the spot test method and the HVE method can distinguish Beta-lactamase activity from acylase activity.

Semi-quantitation of Beta-lactamase activity.

The spot test result for Beta-lactamase activity using a given substrate was classified as weakly positive (W) when the fluorescent intensity of the spot was faint but discernably greater than that of the uninoculated substrate control; and as positive (+) when bright, blue-green fluorescence was observed.

The HVE test result for Beta-lactamase activity using a given substrate was classified as weakly positive (W) when faint fluorescence was observed at the position corresponding to that of the end-product after HVE, and the color intensity of the end-product spot after ninhydrincadmium acetate stain was slightly but discernably greater than that of the end-product in the uninoculated substrate control (produced by spontaneous nonenzymatic hydrolysis during incubation and from end product contamination of commercial sources); as moderately positive (M), when bright, blue-green fluorescence was observed at the position corresponding to that of the end-product but color intensity of the end-product spot after ninhydrin-cadmium acetate stain was less than that of the remaining substrate spot; and as strongly positive (S) when bright, blue-green fluorescence was observed at the position corresponding to that of the end-product spot and the color intensity of the and-product spot after ninhydrin-cadmium acetate stain was greater than that of the remaining substrate spot.

Distribution of Beta-lactamase activities among representative microorganisms.

The spot test method was used for the detection of Beta-lactamase produced by one strain each of *Escherichia coli, E. cloacae, C. freundii, B. cereus* and *B. licheniformis* using ampicillin (for penicillinase activity) and cephalexin (for cephalosporinase activity) as substrates. The results of the spot test shown in FIG. 5A were confirmed by HVE visualized under uv light as shown in FIG. 5B, and with a ninhydrin-cadmium acetate stain as shown in FIG. 6.

Fluorescence was produced by *E. coli* during incubation with ampicillin for 1 h at 37° C. (FIG. 5A), and the end product (D-phenylglycylpenicilloic acid) was detected under uv light (FIG. 5B), and further confirmed by ninhydrin-cadmium acetate stain (FIG. 6). The penicillinase activity of this *E. coli* strain was determined to be weakly positive by both the spot test and the HVE method using the criteria described above, while no cephalosporinase activity was detected by either method.

The fluorescent end-product, D-phenylglycyl-deacetoxycephalosporoic acid, was produced by *E. cloacae* during incubation with cephalexin for 1 h at 37° C. (FIG. 5A). The end-product was visualized under uv light after HVE (FIG. 5B) and further confirmed by ninhydrin-cadmium acetate stain (FIG. 6). The cephalosporinase activity of *E. cloacae* was classified as positive by the spot test and as moderately positive by the HVE method using the criteria described above; no penicillinase activity was detected by either method.

Through use of the spot test and the criteria described above, penicillinase and cephalosporinase activities of *C. freundii* and *B. licheniformis* were both classified as positive, while in *B. cereus*, the penicillinase activity was positive and cephalosporinase activity was negative (FIG. 5A). By the HVE method and the criteria described above, the penicillinase and cephalosporinase activities of *C. freundii* and *B. licheniformis* were both classified as strongly positive; the penicillinase activity and cephalosporinase activity of *B. cereus* was classified as moderately positive and negative, respectively (FIG. 5B and FIG. 6).

Activities of B-lactamases in 21 strains of 7 gram-positive species, and 77 strains of 29 gram-negative species of bacteria were determined by the spot test, the HVE test, and the nitrocefin test after incubation for 1 h at 37° C. (Table 1). The results of the nitrocefin test agreed well with those of the spot test (confirmed by the HVE test). Some Beta-lactamases which acted predominately against ampicillin, such as a few species of gram-positive bacteria, were not detected by the nitrocefin test. Therefore, the fluorescent method disclosed herein was more sensitive than the chromogenic cephalosporin (nitrocefin) method. Activities of Beta-lactamases in selected Beta-lactamase producers listed in Table 1 were further assessed by the rapid spot test and the nitrocefin test after incubation for 5 and 15 minutes at room temperature, the results listed in Table 2. The incubation time needed for a positive reaction for the fluorescent spot test appeared to be about the same as, or shorter than, that needed for the nitrocefin test. Some clinically important microogranisms, such as *N. gonorrhoeae* and *H. influenzae*, produce Beta-lactamases which could be detected by the rapid spot test immediately after the organisms were suspended in the ampicillin substrate solution, without further incubation. The fluorescent spot test detection method described herein can not only distinguish Beta-lactamase activity from acylase activity, but also can detect and differentiate between penicillinase activity and cephalosporinase activity. The fluorescent spot test may require 5 minutes of heating at 120° C. to maximize the fluorescent potential of the end-products, although the mechanism by which heating enhances fluorescence is not fully understood.

The Beta-lactam antibiotic substrate solutions (acid forms) were prepared in 0.04M sodium phosphate buffer, pH 7.5.

These solutions both had a pH of 7.0. The pH of both solutions fell to 6.5 [within the optimal pH ranges of microbial Beta-lactamases (Sykes, R. B., and M. Matthew. Detection, assay and immunology of Beta-lactamases, p. 17–49; J. M. T. Hamilton-Miller and J. T. Smith (ed.), Beta-lactamases, Academic Press, New York 1979], upon compete hydrolysis by *C. freundii*, and could be stored at 4° C. for 5 days or −20° C. for months without detectable increases in fluorescent background as checked by the spot test.

Some organisms fluoresced slightly on paper, but this fluorescence was confined to the center of the applied spot, and could be easily distinguished from the fluorescence of end-products which diffuse radially by capillary action of the paper from the center of application. Therefore, the spot test can be performed without prior removal of the organisms by centrifugation.

Unless the Beta-lactamase sought shows no substrate specificity, the ampicillin and cephalexin substrates should be incubated separately with the organism. When penicillin and cephalosporin substrates are mixed together, the substrate which is not hydrolyzed may act as a competitive inhibitor of the other substrates. For example, *S. marcescens* (strains ATCC 8100 and 17991) exhibit only cephalosporinase activity as detected by the spot test and the HVE test when ampicillin and cephalexin were incubated separately with the organism. However, cephalosporinase activity was not detected in either organism by the spot test or the HVE test when both strains were incubated with a mixture of equal volumes of ampicillin and cephalexin substrate solution for 1 h at 37° C.

The detection method or spot test described herein using ampicillin and cephalexin as substrates, provides a rapid and inexpensive method for the specific detection of microbial Beta-lactamases by detecting the presence of fluorescent end-products. This detection method may have several applications. For example, incubation with human sera can result in a color change for nitrocefin. Therefore, nitrocefin is not suitable for detection of Beta-lactamase in the presence of certain body fluids. It was found that 8 of 8 human sera converted nitrocefin to a red color after 20 minutes incubation at 37° C., but produced no fluorescence after incubation with ampicillin and cephalexin for 1 hr at 37° C. In contrast, the methods described herein have the potential for the direct detection of microbial Beta-lactamases in clinical specimens.

The detection of fluorescent end-products utilizing the method described herein also offers an economical alternative for clinical laboratories which test large numbers of microorganisms for Beta-lactamases. For example, the routine Beta-lactamase tests on staphylococcal isolates using nitrocefin requires a noninhibitory concentration of a semisynthetic penicillin as an inducer for the enzyme. In the present fluorescent spot test method, with sufficient incubation time (e.g., $\geq 15$ min.) ampicillin could serve not only as a substrate, but also as an inducer for these gram-positive bacteria of clinical importance.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

TABLE 1

Activities of β-lactamases of representative microorganisms determined by the spot test, the HVE test, and the nitrocefin test after incubation for 1 h at 37° C.

| Microorganism[a] | β-lactamase activity[b] | | | | |
|---|---|---|---|---|---|
| | Spot test | | HVE test | | Nitrocefin test |
| | P-ase | C-ase | P-ase | C-ase | |
| GRAM-NEGATIVE ENTERIC | | | | | |
| *Citrobacter freundii* | | | | | |

TABLE 1-continued

Activities of β-lactamases of representative microorganisms determined by the spot test, the HVE test, and the nitrocefin test after incubation for 1 h at 37° C.

| | β-lactamase activity[b] | | | | |
|---|---|---|---|---|---|
| | Spot test | | HVE test | | Nitrocefin |
| Microorganism[a] | P-ase | C-ase | P-ase | C-ase | test |
| NRL5329 | + | + | S | S | + |
| ATCC10787 | − | + | − | M | + |
| *Enterobacter aerogenes* NRL9817, ATCC13048 | − | + | − | M | + |
| *Enterobacter agglomerans* NRL9819; ATCC29915 | + | − | S | − | + |
| *Enterobacter cloacae* NRL5335, 9818; ATCC13047 | − | + | − | M | + |
| *Escherichia coli* ATCC21986, 27549, 31027 | W | − | W | − | + |
| *Klebsiella oxytoca* NRL9979 | + | − | S | − | + |
| *Klebsiella pneumoniae* NRL9976; ATCC13883, 27799 | + | − | S | − | + |
| *Morganella morganii* NRL5334; ATCC25830 | W | W | W | W | + |
| *Proteus mirabilis* ATCC14273, 29855 | W | W | W | W | − |
| *Proteus vulgaris* ATCC13315 | W | + | W | M | − |
| *Providencia rettgeri* ATCC9250, 31052 | − | − | − | − | − |
| *Salmonella typhimurium* ATCC13311 | − | − | − | − | − |
| *Serratia marcescens* ATCC8100, 17991 | − | + | − | S | + |
| *Serratia rubidaea* ATCC181 | W | + | W | S | + |
| *Shigella dysenteriae* ATCC13313 | − | W | − | W | + |
| *Shigella sonnei* ATCC11060 | − | + | − | M | + |
| GRAM-NEGATIVE NONENTERIC | | | | | |
| *Branhamella catarrhalis* | | | | | |
| NRL32674, 32681, 32763 | + | + | S | S | + |
| NRL30069, 30071, 32589 | − | − | − | − | − |
| *Eikenella corrodens* ATCC1073, 23834 | − | − | − | − | − |
| *Haemophilus ducreyi* | | | | | |
| V-1157, 1158, 1169 | + | + | S | M | + |
| V-1152, 1168 | − | − | − | − | − |
| *Haemophilus influenzae* | | | | | |
| AS1115, 902 | + | + | S | S | + |
| AS1117, E1a; ATCC19418 | − | − | − | − | − |
| *Neisseria gonorrhoeae* | | | | | |
| NRL33044, 33047, 33050 | + | + | S | S | + |
| NRL8327, 30483, F62 | − | − | − | − | − |
| *Pseudomonas aeruginosa* SM31302-31311 | W | W | W | W | − |
| *Pseudomonas cepaciae* BM1, 2 | + | + | S | S | + |
| *Pseudomonas fluorescens* BM3; ATCC25289 | − | + | − | S | + |
| *Pseudomonas maltophilia* BM4, 5; ATCC13637 | + | + | S | S | + |
| *Pseudomonas putida* BM6, 7; ATCC25571 | − | + | − | S | + |
| GRAM-NEGATIVE ANAEROBIC | | | | | |
| *Bacteroides bivius* ATCC29303 | + | + | S | M | + |
| *Bacteroides capillosus* ATCC29799 | − | − | − | − | − |
| *Bacteroides fragilis* ATCC23745, 25285 | W | + | W | M | + |
| GRAM-POSITIVE | | | | | |
| *Bacillus cereus* | | | | | |
| ATCC13061 | + | − | S | − | + |
| ATCC27348, 14579 | + | − | M | − | − |
| *Bacillus circulans* ATCC4513 | + | − | S | − | − |
| *Bacillus licheniformis* | | | | | |
| ATCC9789, 14409 | + | W | S | W | + |
| ATCC 25972 | + | + | S | S | + |
| *Bacillus subtilis* | | | | | |

TABLE 1-continued

Activities of β-lactamases of representative microorganisms determined by the spot test, the HVE test, and the nitrocefin test after incubation for 1 h at 37° C.

| Microorganism[a] | β-lactamase activity[b] | | | | |
|---|---|---|---|---|---|
| | Spot test | | HVE test | | Nitrocefin test |
| | P-ase | C-ase | P-ase | C-ase | |
| ATCC9799, 14410, 14415 | W | — | W | — | — |
| ATCC14807 | + | — | S | — | — |
| *Staphylococcus aureus* | | | | | |
| ATCC12598, 25923 | — | — | — | — | — |
| BM U17, Su3 | + | — | S | — | + |
| BM Me19 | + | — | S | — | — |
| *Staphylococcus epidermidis* | + | — | S | — | + |
| ATCC12228, 14990 | | | | | |
| *Streptococcus faecalis* | — | — | — | — | — |
| ATCC11420, 12984, 19433 | | | | | |

[a]Strain numbers are those of the American Type Culture Collection (ATCC), the Neisseria Reference Laboratory (NRL), Stephen A. Morse (SM), Barbara H. Minshew (BM), and Arnold L. Smith (AS). Strains of *Haemophilus ducreyi* were described previously (19). The growth conditions for each microorganism were described under "Materials and Methods."
[b]The activities of penicillinase (P-ase) and cephalosporinase (C-ase) in each microorganism determined by the spot test and by the HVE test were recorded as follows: The spot test result for β-lactamase activity using a given substrate was classified as weakly positive (W) when the fluorescent intensity of the spot was faint but discernably greater than that of the uninoculated substrate control; and as positive (+) when bright, blue-green fluorescence was observed. The HVE test result β-lactamase activity using a given substrate was classified as weakly positive (W) when faint fluorescence was observed at the position corresponding to that of the end product after HVE, and the color intensity of the end product spot after ninhydrin-cadmium acetate stain was slightly but discernably greater than that of the end product in the uninoculated substrate control (produced by spontaneous nonenzymatic hydrolysis and from contamination); as moderately positive (M), when bright, blue-green fluorescence was observed at the position corresponding to that of the end product spot but color intensity of the end product spot after ninhydrin-cadmium acetate stain was less than that of the remaining substrate spot; as strongly positive (S) when bright blue-green fluorescence was observed at the position corresponding to that of the end product spot and the color intensity of the end product spot after ninhydrim-cadmium acetate stain was greater than that of the remaining substrate spot.

TABLE 2

Activities of β-lactamases of selected microorganisms determined by the rapid spot test and the nitrocefin test after incubation for 5 and 15 min at room temperature

| Microorganism[a] | β-lactamase activity[b] | | | | | |
|---|---|---|---|---|---|---|
| | Rapid spot test Incubation time | | | | Nitrocefin test Incubation time | |
| | 5 Min | | 15 Min | | | |
| | P-ase | C-ase | P-ase | C-ase | 5 Min | 15 Min |
| GRAM-NEGATIVE ENTERIC | | | | | | |
| *Citrobacter freudii* | | | | | | |
| NRL5329 | + | + | + | + | + | + |
| ATCC 10787 | — | — | — | + | — | + |
| *Enterobacter aerogenes* | — | — | — | + | — | — |
| NRL9817, ATCC13048 | | | | | | |
| *Enterobacter agglomerans* | + | — | + | — | — | + |
| NRL9819; ATCC29915 | | | | | | |
| *Enterobacter cloacae* | — | — | — | + | — | — |
| NRL5335, 9818; ATCC13047 | | | | | | |
| *Klebsiella oxytoca* | + | — | + | — | — | — |
| NRL9979 | | | | | | |
| *Klebsiella pneumoniae* | + | — | + | — | — | — |
| NRL9976; ATCC13883 | | | | | | |
| *Serratia marcescens* | — | — | — | + | — | + |
| ATCC8100, 17991 | | | | | | |
| *Serratia rubidaea* | — | — | — | — | — | — |
| ATCC181 | | | | | | |
| *Shigella sonnei* | — | — | — | + | — | — |
| ATCC11060 | | | | | | |
| GRAM-NEGATIVE NONENTERIC | | | | | | |
| *Branhamella catarrhalis* | + | — | + | — | + | + |
| NRL32674, 32681, 32763 | | | | | | |
| *Haemophilus ducreyi* | + | — | + | — | + | + |
| V-1157, 1158, 1169 | | | | | | |
| *Haemophilus influenzae* | + | — | + | — | + | + |
| AS1115, 902 | | | | | | |
| *Neisseria gonorrhoeae* | + | — | + | — | + | + |
| NRL33044, 33047, 33050 | | | | | | |
| *Pseudomonas cepaciae* | — | — | — | + | — | + |
| BM1, 2 | | | | | | |
| *Pseudomonas fluorescens* | — | — | — | + | — | + |
| BM3; ATCC25289 | | | | | | |
| *Pseudomonas maltophilia* | + | + | + | + | + | + |
| BM4, 5 | | | | | | |
| *Pseudomonas putida* | — | — | — | + | — | + |

TABLE 2-continued

Activities of β-lactamases of selected microorganisms determined by the rapid spot test and the nitrocefin test after incubation for 5 and 15 min at room temperature

| Microorganism[a] | β-lactamase activity[b] | | | | | |
|---|---|---|---|---|---|---|
| | Rapid spot test Incubation time | | | | Nitrocefin test Incubation time | |
| | 5 Min | | 15 Min | | | |
| | P-ase | C-ase | P-ase | C-ase | 5 Min | 15 Min |
| BM6, 7; ATCC25571 | | | | | | |
| GRAM-POSITIVE | | | | | | |
| *Bacillus cereus* | | | | | | |
| ATCC13061 | + | − | + | − | + | + |
| ATCC27348, 14579 | − | − | + | − | − | − |
| *Bacillus circulans* | − | − | W | − | − | − |
| ATCC4513 | | | | | | |
| *Bacillus licheniformis* | | | | | | |
| ATCC9789, 14409 | − | − | + | W | − | + |
| ATCC 25972 | + | − | + | + | + | + |
| *Bacillus subtilis* | − | − | + | − | − | − |
| ATCC14807 | | | | | | |
| *Staphylococcus aureus* | | | | | | |
| BM U17, Su3 | − | − | + | − | − | + |
| BM Me19 | − | − | + | − | − | − |
| *Staphylococcus epidermidis* | | | | | | |
| ATCC14990 | + | − | + | − | + | + |
| ATCC1228 | − | − | + | − | − | + |

[a]Strain numbers are those of the American Type Culture Collection (ATCC), the Neisseria Reference Laboratory (NRL), Barbara H. Minshew (BM) and Arnold L. Smith (AS). Strains of *Haemophilus ducreyi* were described previously (19). The growth conditions for each microorganism were described under "Materials and Methods."
[b]The activities of penicillinase (P-ase) and cephalosporinase (C-ase) in each microorganism determined by the spot test were recorded as follows: The spot test result for β-lactamase activity using a given substrate was classified as weakly positive (W) when the fluorescent intensity of the spot was faint but discernably greater than that of the uninoculated substrate control; and as positive when bright, blue-green fluorescence was observed.

We claim:

1. A rapid method of detecting the presence of Beta-lactamase from microbial sources using a Beta-lactam ring containing substrate whose amide bond is hydrolyzed in the presence of Beta-lactamase, comprising:
   (1) contacting a non-fluorescing substrate which comprising a Beta-lactam antibiotic with an acyl side chain containing an α-amino group and α-phenyl group or a derivative of an α-phenyl group, with either an organism thought to produce Beta-lactamase or a cell-free Beta-lactamase preparation;
   (2) incubating the substrate and the organism or preparation under conditions and for a period of time sufficient to effect hydrolysis of the substrate; and
   (3) determining whether the reaction product between the substrate and either the organism or the preparation fluoresces as a result of Beta-lactamase hydrolysis of said substrate.

2. The method of claim 1 wherein the acyl side chain comprising a D (−)-phenylglycyl side chain or a D (−)-P-hydroxyphenylglycyl side chain.

3. The method of claim 2 wherein D (−)-phenylglycyl side chain is contained within a Beta-lactam antibiotic selected from the group consisting of ampicillin, cephalexin, and cephaloglycin.

4. The method of claim 2 wherein the D (−)-P-hydroxyphenylglycyl side chain is contained within a Beta-lactam antibiotic selected from the group consistng of amoxicillin and cefadroxil.

5. The method of claim 1, including, after step one, incubating the substrate and the organism or the preparation, placing the reaction mixture onto a surface with low background fluorescence, and, after placing the mixture onto the surface, briefly heating the reaction products on the surface to develop fluorescence.

6. The method of claim 5 wherein the surface with low background fluorescence is a sheet material selected from the group consisting of filter paper, cellulose, nitrocellulose, cellulose acetate, silica gel and polyamide.

7. A method of differentiating Beta-lactamase activity from acylase activity, comprising:
   (1) contacting a non-fluorescing Beta-lactam ring containing substrate whose amide bond is hydrolyzed in the presence of Beta-lactamase, the substrate comprising a Beta-lactam antibiotic with an acyl side chain containing an α-amino group and an α-phenyl group or a derivative of an α-phenyl group, with either an organism thought to produce Beta-lactamase or a cell-free Beta-lactamase preparation;
   (2) incubating the substrate and the organism or preparation under conditions and for a period of time sufficient to effect hydrolysis of the substrate; and
   (3) determining whether the reaction product between the substrate and either the organism or the preparation fluoresces, as a result of Beta-lactamase hydrolysis of said substrate, said fluorescence acting as an indicator of the presence of Beta-lactamase activity.

8. The method of claim 7 wherein the acyl side chain comprising a D (−)-phenylglycyl side chain or a D (−)-P-hydroxyphenylglycyl side chain.

9. The method of claim 8 wherein the D (−)-phenylglycyl side chain is contained within an antibiotic selected from the group consisting of ampicillin, cephalexin, and cephaloglycin.

10. The method of claim 8 wherein the D (−)-P-hydroxyphenylglycyl side chain is contained within an antibiotic selected from the group consisting of amoxicillin and cefadroxil.

11. The method of claim 7, including, after step one, incubating the substrate and the organism or the preparation, placing the reaction mixture onto a surface with low background fluorescence, and, after placing the mixture onto the surface, briefly heating the reaction products on the surface to develop fluorescence.

12. The method of claim 11 wherein the surface with low background fluorescence is a sheet material selected from the group consisting of filter paper, cellulose, nitrocellulose, cellulose acetate, silica gel and polyamide.

13. A method of semi-quantitatively determining the amount of Beta-lactamase activity from a microbial source, comprising:
   (1) contacting a non-fluorescing Beta-lactam ring containing substrate whose amide bond is hydrolyzed in the presence of Beta-lactamase, the substrate comprising a Beta-lactam antibiotic with an acyl side chain containing an α-amino group and an α-phenyl group or a derivative of an α-phenyl group, with either an organism thought to produce Beta-lactamase or a cell-free Beta-lactamase preparation;
   (2) incubating the substrate and the organism or preparation under conditions and for a period of time sufficient to effect hydrolysis of the substrate; and
   (3) determining the amount of Beta-lactamase activity as a measure of fluorescence intensity generated as a result of Beta-lactamase hydrolysis of said substrate.

14. The method of claim 13 wherein the acyl side chain comprising a D (−)-phenylglycyl side chain or a D (−)-P-hydroxyphenylglycyl side chain.

15. The method of claim 14 wherein the D (−)-phenylglycyl side chain is contained within an antibiotic selected from the group consisting of ampicillin, cephalexin, and cephaloglycin.

16. The method of claim 14 wherein the D (−)-P-hydroxyphenylglycyl side chain is contained within an antibiotic selected from the group consisting of amoxicillin and cefadroxil.

17. The method of claim 13, comprising, after step one, incubating the substrate and the organism or the preparation, placing the reaction mixture onto a surface with low background fluorescence, and, after placing the mixture onto the surface, briefly heating the reaction products on the surface to develop fluorescence.

18. The method of claim 17 wherein the surface with low background fluorescence is a sheet material selected from the group consisting of filter paper, cellulose, nitrocellulose, cellulose acetate, silica gel and polyamide.

19. A method of differentiating between the presence of penicillinase and cephalosporinase from microbial sources, comprising:
   (1) contacting a non-fluorescing penicillinase substrate with an acyl side chain containing an α-amino group and an α-phenyl group or a derivative of an α-phenyl group with either an organism thought to produce Beta-lactamase, or a Beta-lactamase preparation;
   (2) incubating the substrate and the organism or preparation in step 1 under conditions and for a period of time sufficient to effect hydrolysis of the substrate;
   (3) determining whether the reaction product between the penicillinase substrate and either the organism or the preparation fluoresces as a result of Beta-lactamase hydrolysis of said substrate;
   (4) contacting a non-fluorescing cephalosporinase substrate with an acyl side chain containing an α-amino group and an α-phenyl group or a derivative of an α-phenyl group with the same organism or preparation used in step 1;
   (5) incubating the substrate and the organism or preparation in step 4 under conditions and for a period of time sufficient to effect hydrolysis of the substrate; and
   (6) determining whether the reaction product between the cephalosporinase substrate and either the organism or the preparation fluoresces as a result of Beta-lactamase hydrolysis of said substrate.

20. The method of claim 19 wherein the acyl side chain comprising a D (−)-phenylglycyl side chain or a D (−)-P-hydroxyphenylglycyl side chain.

21. The method of claim 20 wherein the D (−)-phenylglycyl side chain is contained within an antibiotic selected from the group consisting of ampicillin, cephalexin, and cephaloglycin.

22. The method of claim 20 wherein the D (−)-P-hydroxyphenylglycyl side chain is contained within an antibiotic selected from the group consisting of amoxicillin and cefadroxil.

23. The method of claim 19, comprising, after step one, incubating the substrate and the organism or the preparation, placing the reaction mixture onto a surface with low background fluorescence, and, after placing the mixture onto the surface, briefly heating the reaction products on the surface to develop fluorescence.

24. The method of claim 23 wherein the surface with low background fluorescence is a sheet material selected from the group consisting of filter paper, cellulose, nitrocellulose, cellulose acetate, silica gel and polyamide.

25. A method of detecting the fluorescent end-product initiated by the presence of Beta-lactamase activity within a culture medium without removal of the bacteria from the milieu, comprising:
   impregnating an interface layer with a non-fluorescing Beta-lactam ring containing substrate with an acyl side chain containing an α-amino group and an α-phenyl group or a derivative of an α-phenyl group, whose amide bond is hydrolyzed in the presence of Beta-lactamase;
   placing the interface layer containing said substrate in contact with the bacteria on the culture medium; and
   determining whether the reaction product between the substrate and the bacteria fluoresces as a result of Beta-lactamase hydrolysis of said substrate.

26. The method of claim 25 comprising, after contacting the interface layer with the culture medium, incubating the layer and medium to develop fluorescence.

27. The method of claim 25 wherein the interface layer is any nonfluorescing sheet material.

* * * * *